US00RE34293E

United States Patent [19]

Goble et al.

[11] E Patent Number: Re. 34,293

[45] Reissued Date of Patent: Jun. 22, 1993

[54] LIGAMENT ATTACHMENT METHOD AND APPARATUS

[76] Inventors: E. Marlowe Goble, 1414 E. 1220 North; W. Karl Somers, 651 N. 150 West, both of Logan, Utah 84321

[21] Appl. No.: 529,319

[22] Filed: May 29, 1990

Related U.S. Patent Documents

Reissue of:

[64] Patent No.: 4,772,286
Issued: Sep. 20, 1988
Appl. No.: 15,432
Filed: Feb. 17, 1987

[51] Int. Cl.[5] ..... A61F 1/00

[52] U.S. Cl. ..... 623/13

[58] Field of Search ..... 623/13, 16; 606/72, 606/73, 80, 88, 96, 97

[56] References Cited

U.S. PATENT DOCUMENTS

| | | | |
|---|---|---|---|
| 4,301,551 | 11/1981 | Dore et al. | 623/13 |
| 4,467,478 | 8/1984 | Jurgutis | 623/13 |
| 4,483,023 | 11/1984 | Hoffman, Jr. et al. | 623/13 |
| 4,590,928 | 5/1986 | Hunt et al. | 623/13 X |
| 4,597,766 | 7/1986 | Hilal et al. | 623/13 |
| 4,605,414 | 8/1986 | Czajka | 623/13 |
| 4,712,542 | 12/1987 | Daniel et al. | 623/13 X |
| 4,823,780 | 4/1989 | Odensten et al. | 606/96 |

*Primary Examiner*—David Isabella

*Attorney, Agent, or Firm*—M. Reid Russell

[57] ABSTRACT

The invention provides a system for surgically implanting an allograft or prosthetic ligament as a replacement for a patient's cruciate ligaments. In a practice of the system, as a replacement for an anterior cruciate ligament, the patient's leg is bent and maintained at approximately a ninety degree (90°) angle, a single incision is made medial to the tibial tuberosity, From this incision, under fluoroscopic and arthroscopic control, a guidewire is driven through the tibia and across the cruciate ligament junctions with the proximal tibia and distal femur ends and into the femur cortex. Succesively larger drills are then turned along the guidewire to form a ligament tunnel, with, as a last step in the tunnel formation process, the preparation of the femur cortex end of the tunnel to receive a femoral connector of the implanted ligament, which connector is arranged in one embodiment to be outwardly flared and in another embodiment to be turned into the appropriately prepared femur end of the ligament tunnel to lock therein. The invention, in addition to the embodiment of the ligament femur end connectors, further includes a tibial surface ligament tibial end connector for both securing the ligament end to the bone and the setting ligament tensioning, of which ligament connectors can be manufactured from a biodegradable material for absorption by the body.

35 Claims, 4 Drawing Sheets

LIGAMENT ATTACHMENT METHOD AND APPARATUS

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to surgical implants and more particularly, to surgical procedures and appliances for intraarticular anterior and posterior ligament reconstruction.

2. Prior Art

It is well known by anyone who has participated in athletics that the human knee is injury prone, particularly from lateral forces applied thereto. Where the knee joint is considered by most laymen to be essentially a hinged joint, in reality it provides a complicated mechanical movement that would be nearly impossible to duplicate with present technology. In operation, the human knee joint permits movement of flexion and extension in certain positions and even provides for a slight inward and outward rotation. Considering only movement of flexion and extension, the mechanical actions that take place in such movement include a certain amount of gliding and rotation along with the hinge action such that the same part of one articular surface of the distal fem ur or proximal tibia will not always be applied to the same part of the other articular surface, and the axis of motion is not fixed. In fact, if the knee joint is examined while a condition of extreme flexion, the posterior part of the articular surfaces of the tibia will be found to be in contact with the fem ur posterior around the extremities of the condyles. Whereas, if the movement was simple hinge like movement, the axis around which the revolving movement of the tibia would occur should be in the back part of the condyle. With the same leg brought forward into a position of semi-flexion, the upper surface of the tibia will seem to glide over the condyle of the fem ur, such that the middlepart of the articular facets are in contact, and the axis of rotation is therefore shifted forward to near the center of the condyle. When the leg is brought into the extended position, still further gliding takes place as does a further shifting forward of the axis of rotation. Knee joint flexure and extension is therefore not a simple movement but is accompanied by a certain amount of outward rotation around a vertical axis drawn through the center of the head of the tibia. This rotation is due to the greater length of the internal condyle, and to the fact that the anterior portion of its articular surface is inclined obliquely outward. In consequence, toward the close of the movement of extension, just before complete extension, the tibia will glide obliquely upward and outward over the oblique surface of the inner condyle, and the leg will be necessarily rotated outwardly. In flexation of the joint, the converse of these movements takes place, the tibia gliding backwardly around the end of the fem ur, at the commencement of which movement, the tibia is directed downward and inward along the oblique curve of the inner condyle, thus causing an inward rotation to the leg.

The above sets out a brief summary of knee joint functioning that takes place in knee flexure and extension. It is provided to show that this functioning is far more than a hinge movement and involves inward and outward rotation. It should be apparent therefore that in a repair of one or more ligaments of the knee, particularly in an intraarticular anterior and posterior ligament reconstruction that involves the cruciate ligaments, it is of significant value that the replacement ligaments, either a graft or proshetic ligament, be fitted so as to, as nearly as possible, duplicate the positioning of the natural ligament. Heretofore, procedures and devices for use in preparing damaged ligaments, particularly the cruciate ligaments, have generally involved attaching the ligament device across the knee at the juncture of the distal fem ur and proximal tibia surfaces. Where an attempt has been made to replace a cruciate ligament that involves securing the replacement ligament ends to the points on the opposing bone surfaces where that natural ligament was attached, such procedure has involved extensively opening the patient's knee area and/or forming intersection tunnels through the respective tibia and fem ur ends and positioning a ligament therebetween. An example of such surgical technique and an implant device is shown in a patent by Hunt, et al., U.S. Pat. No. 4,590,928. This patent is directed to an implant and kit therefore but does not, as does the present invention, provide an arrangement that is a near duplication for the patient's natural ligament. Rather, the Hunt, et al. patent is devoted to connectors and an implant that incorporates carbon fibers and, where tunnels are shown formed in the respective bones, such are apparently formed where access is convenient. As the tunnels are not aligned and each is open to without the fem ur and tibia surfaces, their formation involves extensive opening of the knee to provide access to the bone surfaces. Unlike the Hunt, et al. patent procedure, the present invention provides for ligament reconstruction using essentially an arthroscopic technique where a single incision only is made to the bone below the tibia tuberosity. Form that point, a tunnel is formed into the bone that passes through the respective points of connection of a cruciate ligament between the proximal tibia and distal fem ur and into the fem ur cortex. The fem ur cortex is then prepared to receive a ligament end coupling fitted therein to secure one ligament end.

Earlier ligament replacement procedures have involved an extensive opening of the knee and have included forming passages or tunnels in the tibia and fem ur from the bone surfaces wherethrough are pulled a natural or artificial ligament, the ends of which ligament are bent and secured as with staples to the bone surfaces. Unlike such earlier procedures and arrangements, the present invention provides for both fitting a ligament to extend across the knee so as to most nearly duplicate the natural ligament positioning and provides for internal coupling the one ligament within a bone cortex. Additionally, the present invention provides a convenient arrangement for adjusting the implanted ligament tensioning to most nearly duplicate a natural condition. The present invention therefore provides both a unique surgical approach and attachment devices to produce and implant that most nearly duplicates the patient's natural ligament arrangement tham has heretofore been possible.

BRIEF SUMMARY OF THE INVENTION

It is therefore a primary object of the present invention to provide an arthroscopic system or technique for replacing with an allograft or prosthetic ligament a ruptured ligament of the knee, preferably a cruciate ligament.

It is another of the present invention to provide an arthroscopic procedure that employs a single incision only that is made medial to the patient's tibial tuberosity and at this point tunneling through the bone, across the distal fem ur and proximal tibial surfaces and into the fem ur cortex, the tunnel to pass through the points of connection of the ligament ends to the bone of either the anterior or posterior cruciate ligament.

It is another object of the present invention to provide for forming the tunnel to end in the femoral cortex just beyond the medullary channel and to prepare it to receive a connector that is turned or expanded therein so as to positively lock a ligament end within that bone cortex. It is another object of the present invention to provide a procedure for tunneling through the patient's tibia across the proximal tibial and distal fem ur surfaces and into the fem ur cortex that involves opening the patient's knee at a single point or location only on the tibial tuberosity and for closely controlling the tunnel formation through a use of fluoroscopic and/or arthroscopic procedures to form a passage that is essentially straight and intersects the connection points of the ruptured cruciate ligament on the bone surfaces so as to receive an allograft or prosthetic ligament that is fixed on one end within the fem ur cortex and extends from the tunnel end at the tibial tuberosity.

Still another object of the present invention is to provide an end coupling for the prosthetic ligament to secure it at the tunnel entrance at the tibial tuberosity and adjusting the ligament tensioning.

Still another object of the present invention is to provide a surgical procedure for replacing a torn or damaged cruciate ligament with an allograft or prosthetic ligament that requires minimal patient trauma and minimizes the time required for healing.

Still another object of the present invention is to provide an allograft or prosthetic ligament for replacement of a ruptured or damaged ligament that includes connectors made of a biodegradable material for maintaining the ligament in place and will be absorbed by the body in the healing process.

In accordance with the above objects, the present invention is in an arthroscopic surgical procedure for installation of an allograft or prosthetic ligament as a replacement for a ruptured knee ligament, preferably either an anterior or posterior cruciate ligament. In a practice of the procedure, a patient's lower leg is maintained in approximately a ninety degree (90°) angle to their upper leg and a longitudinal incision is made medial to the tibial tuberosity, which incision is made to the bone. At that incision, a stainless steel guidewire is driven in the anterior medial tibia at a point that is approximately two (2) centimeters distance to the medial tibial plateau. Guidewire insertion is conducted under flurorscopic and arthroscopic control. The guidewire, after insertion, is thereby visualized as it is forced through the joint of the distal fem ur and proximal tibia, crossing the intercondylar notch area of the knee to engage the posterior and lateral femoral condyle. The preferred point of fem ur entry is deep within the intercondylar notch, as identified under fluoroscopic visualization, approximately four (4) millimeters anterior to the junction of the fem ur posterior cortex and the intercondylar seam as would be seen in a true lateral x-ray film of the distal fem ur. Guidewire travel is continued to pass through the fem ur cancellous bone, the medullary channel and into the anterior lateral cortex so as to be just proxim al to the metaphysical flare of the distal fem ur. So installed, the guidewire is then used to direct drill points of increasing drill sizes along its course, the drilling operation to sequentially increase the passage or tunnel diameter from the tunnel entry at the tibial tuberosity.

In the passage or tunnel form ation the increasing size drills are stopped in the medullary channel. As a final step in the tunnel formation, the tunnel end is drilled beyond the medullary channel into the fem ur anterior cortex where the guidepin has been lodged. This final hole is made in preparation for turning either a tap therein forming threads or a flaring drill to widen that tunnel end. In one embodiment the ligament femoral end connection is a threaded component to be turned into the threaded tunnel end. In another embodiment the ligament femoral end connector is arranged to be expanded or outwardly flared to fill the widened tunnel end.

After tunnel formation, the ligament is inserted to where its end is secured in the fem ur cortex as by either turning or expanding the connector end therein. The ligament thereby extends from its cortex end to where it exits the tunnel at the tunnel point of entry on the tibial tuberosity. Where the ligament is an allograft, the ligament end can be bent at the tunnel end across the bone and stapled thereto. Where the ligament is a prosthetic ligament, a preferred end coupling involves forming threads in the ligament end to receive a flat disk that is center tapped and slopes outwardly from one face to the other around the circumference, the small diameter face to nest in the tunnel end. This connector arrangement provides a capability for ligament length adjustment to achieve a desired ligament tensioning. In both embodiments, the respective connectors can be formed of a biodegradable material, such as a polylactic acid that will be absorbed by the body during the healing process, the bone growing to either the prosthetic or allograft ligaments.

Utilization of the above-described ligament and preferred connector installing procedure provides for ligament positioning to most nearly duplicate a damaged ligament and for setting a desired tensile stress in the ligament.

DESCRIPTION OF THE DRAWINGS

In the drawings that illustrate that which is presently regarded as the best mode for carrying out the invention.

DETAILED DESCRIPTION

The present invention is in a surgical process or system whereby, from a single incision only made in a patient to their tibial tuberosity, a straight passage or tunnel is formed that will cross the proximal and distal fem ur surfaces and extend into the fem ur cortex. The tunnel is for receiving a ligament, either allograft or prosthetic, that is secured therein by one of several ligament end attachment embodiments of the invention. The process is primarily directed to but should be understood is not limited to replacement of a patient's damaged anterior or external cruciate ligament. The present procedure is described herein with respect to a replacement of the amterior cruciate ligament that is the ligament that is attached on its one end to the depression in front of the spine of the tibia and is part of the external semi-lunar fibrocartilage and is arranged to pass obliquely upwardly as well as backwardly and outwardly therefrom. The other ligament end is joined onto the inner and back part of the fem ur outer condyle. The anterior cruciate ligament, during leg rotation, is in a semi-flexed condition, and opposes inward rotation. It is this ligament that, in athletic play where the knee is subjected to an inward force, such as football, is most often dam aged. Heretofore, repair of the anterior cruciate ligament has involved an extensive surgical opening of the knee along with a release of the outer ligaments and cartilage that surround the tibia to effectively lay open the knee. Whereafter, the ruptured ligament has been repaired, if possible or replaced with an allograft or prosthetic ligament. Where replacement is in order, the procedure has involved tunneling through the fem ur and tibia, the tunnel exiting both bone surfaces, and a stapling of the ligament ends of the bone surfaces. Such procedure has required that the patient's leg be immobilized for an extended period of time to allow for healing, and, generally a full restoration of the patient's knee has not been obtained. Even in the best of circumstance, after a long restorative or healing period, extensive physical therapy is necessary to restore the knee to proper functioning. Unique to such former procedures the present invention provides a reconstructive procedure for arthroscopic insertion of either an allograft or prosthetic ligament that involves a single sm all incision only and provides, with a successful completion of the procedure, a ligament that is essentially ready for use.

Figure 1:
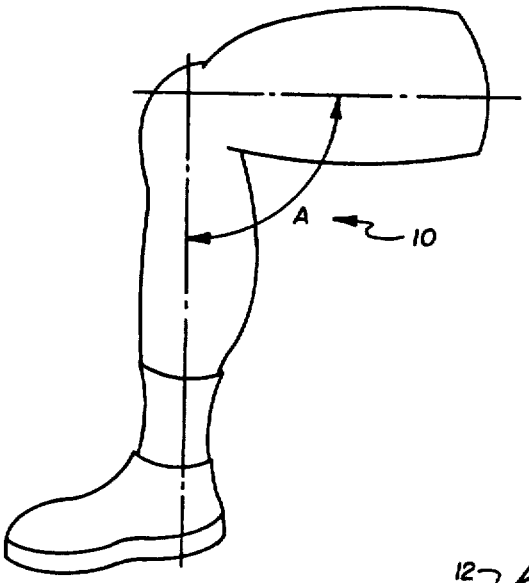
FIG. 1 shows a patient's leg with their lower leg maintained at approximately a ninety (90°) angle to the upper leg, which positioning is to be maintained throughout a surgical procedure of the present invention.

FIG. 1 shows that in a practice of the arthroscopic procedure of the present invention for replacement of the amterior cruciate ligament, the patient's leg 10 is preferably maintained at approximately a ninety degree (90°) angle between the fem ur and tibia. W ith the leg 10 so maintained, a longitudinal incision of approximately five (5) centimeters is made in the lower leg just below the external semi-lunar fibrocartilage to open the skin to the tibial tuberosity. At this exposed bone section, the end of a stainless steel guidewire, not shown, is positioned on a point of the tibial tuberosity that is approximately two (2) centimeters distal to the medial tibial plateau. The guidewire is then urged into that bone mass at that point by an application of a force thereto as by hammering the opposite guidewire end, or the like. This insertion process is made under fluoroscopic control to allow a surgeon to follow the guidewire progress through the bone so as to ensure that it will exit a point on the proximal tibia surface where the anterior crucial ligament is connected to the tibia and is blended with the semi-lunar fibrocartilage. This point will be approximately two (2) centimeters posterior to the most anterior border of the tibial plateau. Guidewire travel to verify its positioning as it enters the joint after piercing the tibial connection of the anterior cruciate ligament can also be visualized arthroscopically through an opening made in the knee cap area.

Guidewire travel can thereby be observed both arthoscopically and fluoroscopically, insuring that it travels across the intercondylar notch area of the knee to engage the posterior and lateral femoral condyle at a point that is deep within the notch. This point is approximately where the opposite end of the anterior crucial ligament attaches to the fem ur at the intercondylar notch area. It is generally located approxim ately four (4) millimeters anterior to the junction of the fem ur posterior cortex and the intercondylar seam as would be seen in a true lateral x-ray film of the distal fem ur. During this procedure, as set out above and shown in FIG. 1, the knee is maintained or fixed in a ninety degree (90°) position to ensure that the formed passage will be essentially straight and that points of engagement of the guidewire with the ends of the anterior crucial ligament will be optimal.

After verifying that the guidewire pointed end is properly located on the junction of the fem ur posterior cortex and the intercondylar seam, it is further forced into the bone mass. The guidewire is driven through the cancellous bone that surrounds the medullary channel to pass through that medullary channel and into the fem ur amterior lateral cortex to a point that is just proximal to the metaphysical flare. Guidewire positioning is again verified radiologically and is thereafter utilized to guide drill points of increasing sizes along the guidewire course. Such drilling begins at the entry point on the anterior medial tibia and terminates at the fem ur medullary channel before the anterior lateral cortex. The drill points that are selected for forming the tunnel to receive a prosthetic ligament preferably begin at five sixteenths of an inch (5/16") and are progressively increased in size by one sixteenth of an inch (1/16") increments to approximately seven sixteenths of an inch (7/16") in diameter. In practice, it is preferred that the tunnel is not drilled beyond the fem ur medullary channel so as not to dislodge the guidewire end lodged in the anterior cortex. For forming a tunnel to receive an allograft ligament, the above described procedure is employed, except that the preferred drill sizes begin at six (6) millimeters and progress to eight (8) millimeters as the tunnel is enlarged.

After the required diameter of hole or tunnel is formed that is suitable for the selected ligament, a final drilling step is the insertion of a one quarter of an inch (¼") canulated drill into the tunnel to pierce the anterior lateral cortex of the fem ur. This step is in preparation for fitting a tap or flaring drill into that cortex. With this drilling step the guidewire is released and can be removed. The tunnel end in the fem ur anterior lateral cortex is then ready to be prepared to receive a femoral attachment end of either allograft or prosthetic ligament to be secured therein. For a threaded end coupling the anterior lateral cortex will preferably be tapped to approximately a three eights of an inch (⅜") diameter. While, for a skirted end coupling as will be described later herein, the tunnel end receives a flaring drill turned therein.

Figure 2:
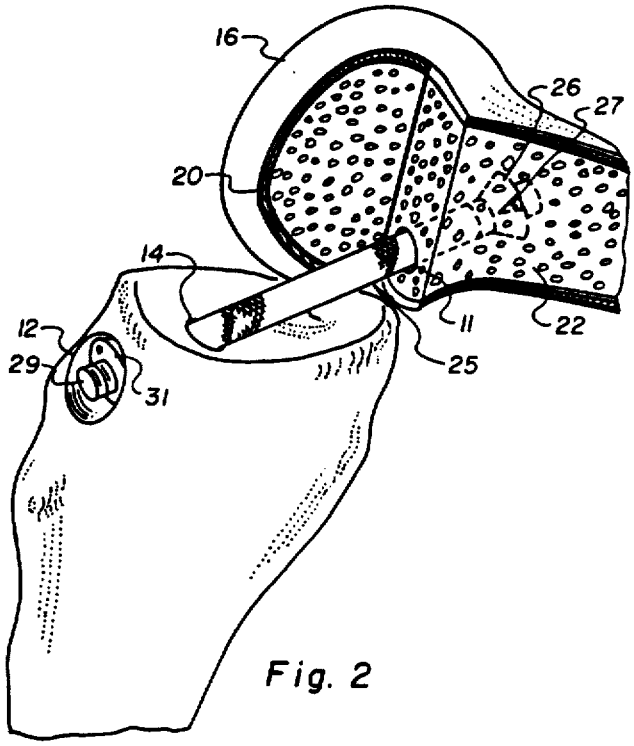
FIG. 2 is an enlarged side elevation view exposing the proximal tibia and distal fem ur ends of the leg of FIG. 1, which distal fem ur is shown as having had a section removed to the bone cortex, exposing a tunnel formed therein that contains one embodiment of a prosthetic ligament and end connectors therefore of the present invention.
Figure 3:
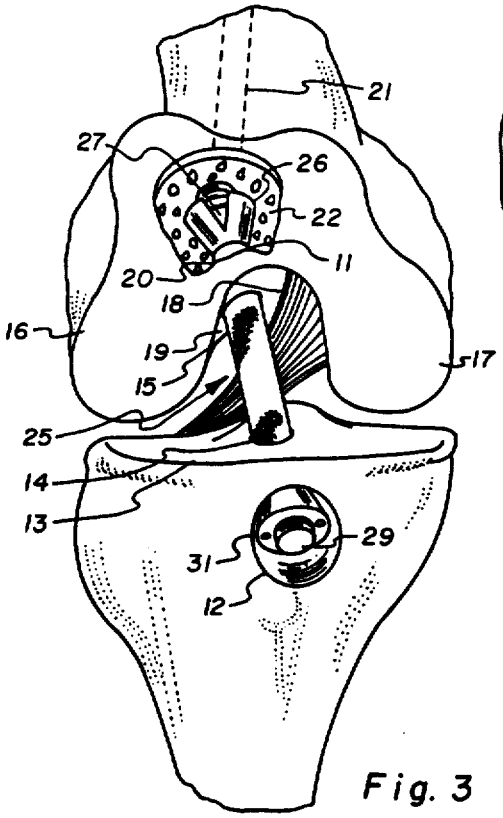
FIG. 3 is a front elevation view of the distal fem ur and proximal tibia ends of FIG. 2 showing a portion of the fem ur cortex removed exposing the tunnel with the prosthetic ligament end secured therein.

With the tibia maintained at a ninety degree (90°) angle to the fem ur, FIGS. 2 and 3 show tunnel 11 formed between the distal fem ur and proximal tibia ends and show a section of the fem ur removed therefrom. The Figs. illustrate the positioning of the respective bone ends and show a prosthesis ligament secured therein. Tunnel 11 exits the proximal tibia at a point 14 that is approximately two (2) centimeters posterior to the most anterior border of that tibial plateau 13 and is approximately the connection point of the end of the anterior cruciate ligament to the bone surf ace. The intercondylar notch area, shown at 15 in FIG. 3, is the point of entry of tunnel 11 into the distal fem ur, the tunnel passing between the posterior and lateral femoral condyles 16 and 17. The preferred tunnel entry point is on the distal fem ur is determined radiologically and should be appropriately four (4) millimeters anterior of the juncture of the fem ur posterior cortex 18 and the intercondylar seam 19. From this point of entry the tunnel 11 passes through the cancellous bone 20 and through the medullary channel 21, as shown in broken lines, and terminates in the anterior lateral cortex 22.

A practice of the above set out procedure therefore will produce a tunnel suitable for receiving a ligament to replace the anterior cruciate ligament as shown in FIGS. 2, 3, 7, and 11, with the tunnel end that terminates in the cortex to receive a ligament end connector secured therein, as will be discussed in detail hereinbelow. It should, however, be understood that, with appropriate changes to the tunnel point of entry and angle of travel therethrough it can be formed to pass through the junctions of the posterior cruciate ligament with the respective bone surfaces within the scope of this disclosure.

Figure 5A:
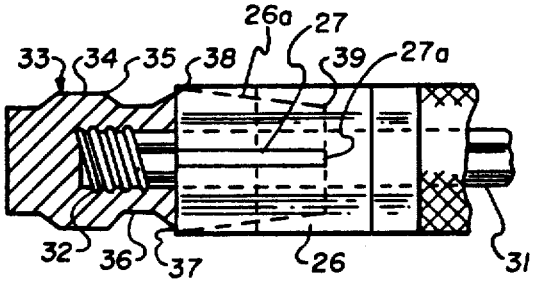
FIG. 5A is an enlarged end view of the femoral attachment end of the prosthetic ligament of FIG. 4.
Figure 5B:
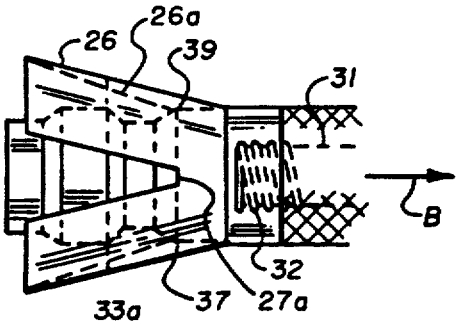
FIG. 5B is a view like FIG. 5A except that it shows the femoral attachment end having been expanded to the flared configuration shown in FIGS. 2 and 3.

FIGS. 2 and 3 illustrate a first embodiment of an expandable cone 26 as a femoral attachment end for a prosthetic ligament 25. The expandable cone 26 is cylindrical in shape and preferably includes longitudinal slots 27 formed at spaced intervals therearound. So arranged, the cone end can be expanded to the attitude shown in FIGS. 2 and 3 when an expansion anchor 33 is pulled therein, the cone end breaking at longitudinal slots 27 to form a skirt. To accommodate the cone 26 that has been flared into a skirt, as shown also in FIG. 5B, the femoral end of tunnel 11 must also be outwardly flared at its most distant point. From the flared portion, the tunnel to taper a lesser radius or circumference that is essentially the ligament radius. For forming such outwardly flared tunnel end portion, a drill that is shown in an earlier application for U.S. patent application, Ser. No. 845,929, that the present inventor is a coinventor of, is preferred. Such drill includes sissoring blades that, at a certain depth of penetration of the drill end relative to a guide sleeve thereof, will pivot apart. With the sissoring blades flaring outwardly, the drill will then cut an inverted skirt shaped hole at the tunnel end to accommodate the prosthetic ligament expandable cone 26 after it has been flared outwardly therein. While a drill like that described in the aforesaid earlier application for U.S. patent is preferred, it should be understood that other drill arrangements for forming an inverted skirt or like enlarged femoral end of tunnel 11 can be so used within the scope of this disclosure.

Figure 4:
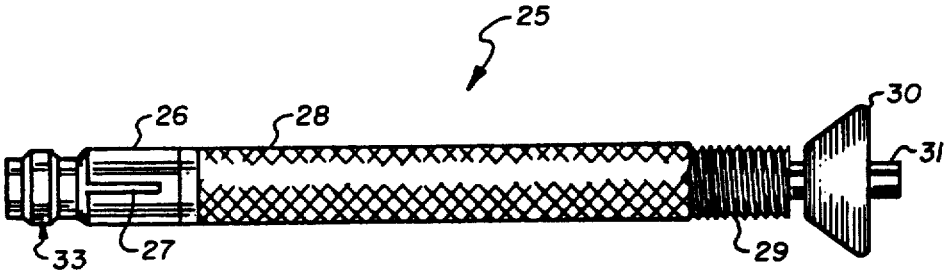
FIG. 4 shows an enlarged side elevation view of the prosthetic ligament of FIGS. 2 and 3 removed from the patient's knee, and shows the ligament femoral and tibial attachment ends as they appe ar before installation.

FIGS. 2, 3, and 4 show the prosthetic ligament 25, shown to be preferably formed from a braided fabric and includes as the femoral attachment end, the expandable cone 26. The expandable cone 26 is preferably attached to the prosthetic ligament 25 in the manufacturing process. The opposite end of ligament 25 is shown threaded therealong at 29 for receiving, as a tibial attachment end, a flattened cone 30. Flattened cone 30 is holed and threaded longitudinally therethrough to be turned over the threaded prosthetic ligament tibial end 29. The flattened cone outer circumference is shown to appear outwardly from the edge of one face to the edge of the other face with the lesser diameter cone face to wedge in tunnel 11 open end. To provide for expanding cone 26, as shown best in FIG. 4, the prosthetic ligament 25 includes a longitudinal passage that is open therethrough and receives an inner shaft 31 telescoped to slide therein. The inner shaft 31, as illustrated best in FIGS. 5A and 5B, included a threaded end 32 that is for turning into a threaded central opening in a flat face of an expansion anchor 33. The expansion anchor 33 is shown to have, opposite to the flat face, a cylindrical nose and is flared or tapered outwardly back from the nose end into a cylindrical center section 34. Back therefrom the anchor tapers inwardly from an end edge 35 into a saddle 36 and then flares outwardly from 37 to terminate in a rear edge 38. The anchor rear edge 38 is aligned with the expanding cone 26 open end to travel therein. The cone 26 is tapered inwardly from a widest point at its open end, the opening therethrough reducing in diameter, as illustrated in broken lines at 26a in FIGS. 5A and 5B to a continuous groove 39 formed around the cone inner circumference at approximately the closed ends 27a of longitudinal slots 27. As shown best in FIG. 5B, pulling the expansion anchor 33 into the expandable cone 26 causes that cone end to expand outwardly, flaring the cone at longitudinal slot ends 27a. With continued travel of the expansion anchor therein the anchor rear edge 38 will engage and seat in groove 39 having flared the cone 26, as shown in broken lines in FIG. 5B, locking the expansion anchor therein. Shaft 31 travel to so move expansion anchor 33 into the expandable cone 26 is shown by the arrow B in FIG.

5B. So arranged, travel of the anchor within the expandable cone 26 causes it to break at the slot 27 end 27a flaring the cone end outwardly into a flattened cone. The expandable cone 26 is thereby erected to have to its greatest diameter at its rearmost point the tunnel 11, that cone flared portion filling the tunnel end and permanently seating therein. This coupling has been found in pull-out tests performed thereon to resist separation at forces in excess of 1300 neutrons that is estim ated to be a maximum force as could reasonably be expected to be exerted on the ligament.

Figure 6:
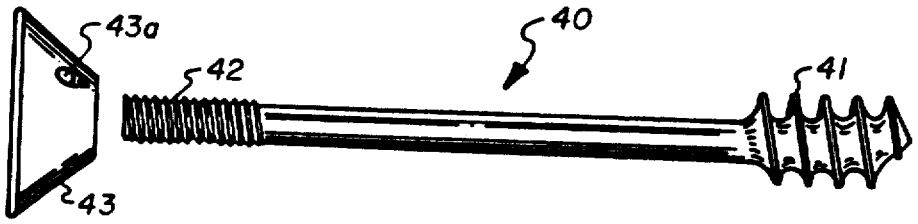
FIG. 6 shows another embodiment of a prosthetic ligament that incorporates a deep threaded end as the femoral attachment end and includes the threaded tibial attachment end that is like shown in FIGS. 2 through 4.

FIG. 6 shows another embodiment of a prosthetic ligament 40 that includes, as a femoral attachment end, deep threads 41 that are formed in the ligament femoral end. These threads are preferably formed during the fabrication thereof as are smaller machine threads 42 that are formed in the ligament tibial attachment end. Threads 41, as illustrated, are preferably cut deep and wide to bite deeply into the tunnel femoral anterior cortex end, which threads are cut or formed therein, as set out hereinabove, as a last step in the tunnel formation process. As with the description of prosthetic ligament 25, the machine threads 42 that are formed as the tibial attachment end are to receive a flattened cone 43 turned thereover. In the prosthetic ligament 25 and 40 embodiments the tibia attachment component is preferably the flattened cone shaped collar that is longitudinally center threaded therethrough for turning over the threaded prosthetic ligament threaded end such that the cone lesser diameter end will travel into the tibia tunnel 11 end. Flattened cone 43 turning is preferably accomplished by fitting a tool, not shown, into a hole or holes 43a that extend through the cone to the greater diameter face thereof, and turning the collar with that tool. This arrangement provides for adjusting ligament tension by appropriately turning the collar on the ligament to engage the tibia tunnel end.

Figure 7:
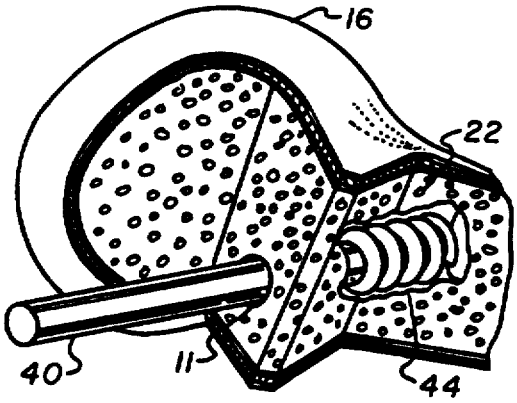
FIG. 7 is a side elevation view of a distal fem ur showing a section removed so as to expose the bone cortex and shows the ligament femoral attachment end of FIG. 6 turned into a tapped tunnel end.

As set out hereinabove, the tunnel 11 femoral end, after it has been tapped or otherwise machined to form threads therein, accommodates the threaded end 41 of prosthetic ligament 40 turned therein. This tapping or threading can be accomplished by insertion of the canulated drill into the fem ur anterior lateral cortex end of tunnel 11, as described hereinabove, followed by a tap turned therein. Such tap is inserted along the prepared tunnel 11 and is turned to tap that fem ur anterior cortex at 44, as illustrated in FIG. 7. Whereafter, the prosthetic ligament 40 of FIG. 6 is turned into the tunnel end 44, as illustrated in FIG. 7, to where the ligament end butts against the tunnel end, locking the ligament therein. Thereafter, prosthetic ligament length and tension adjustment is accomplished, as set out above, by turning the flattened cone 43 on the prosthetic ligament thread end 41, to where it engages the tibia end of tunnel 11. Setting prosthetic ligament tension is preferably accomplished while maintaining the patient's leg 10 in the attitude shown in FIG. 1.

Figure 8:
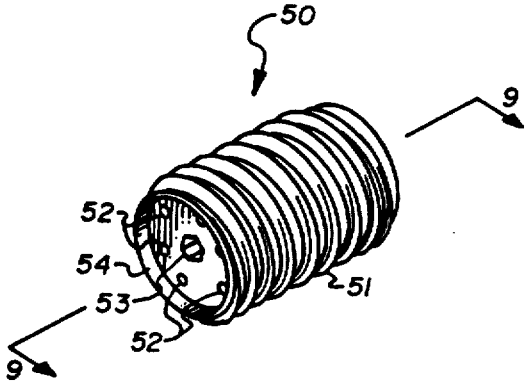
FIG. 8 shows a profile perspective view of a threaded cylindrical allograft ligament end connector that is for turning into a tapped tunnel end in the fem ur cortex.
Figure 9:
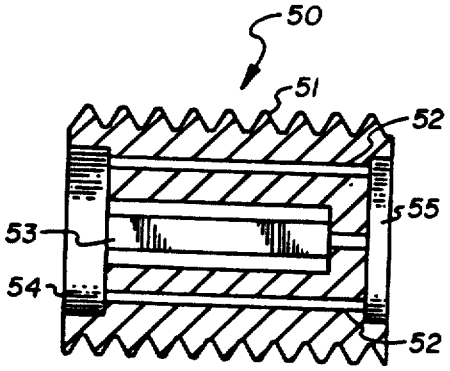
FIG. 9 shows a sectional view taken along lines 9—9 of the end connector of FIG. 8.
Figure 10A:
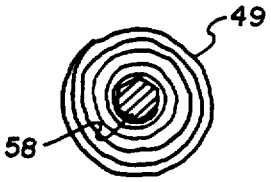
FIG. 10 shows the end connector of FIG. 9 being sewn onto the end of an allograft ligament and shows a hex-sided driver fitted into a like sided longitudinal hole in that end connector with the allograft ligament wrapped therearound.
Figure 10:
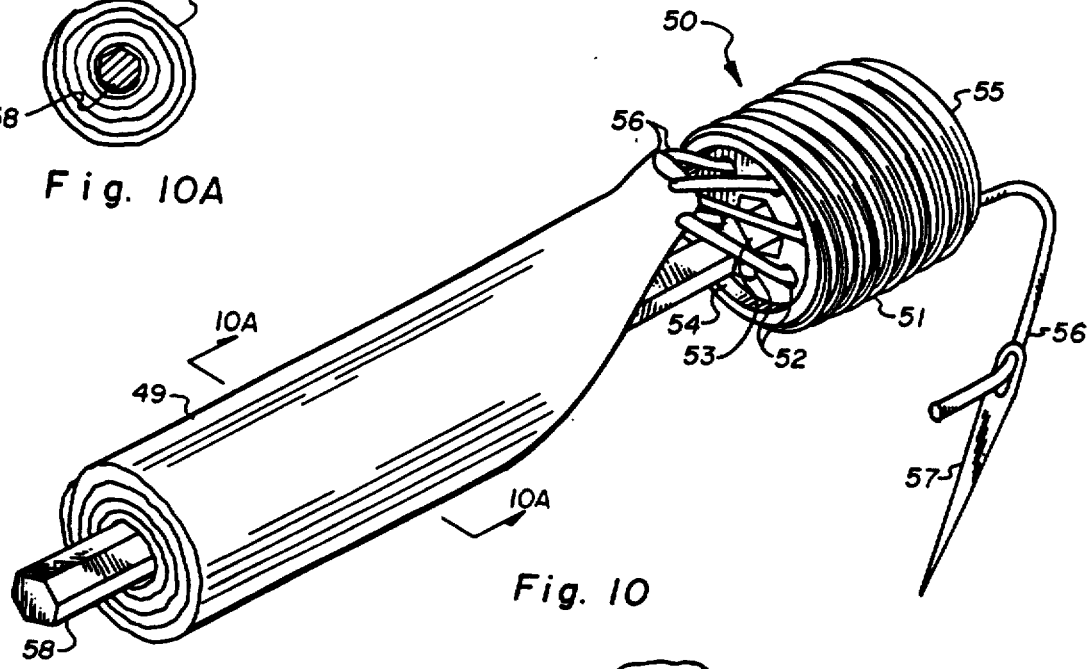
Figure 11:
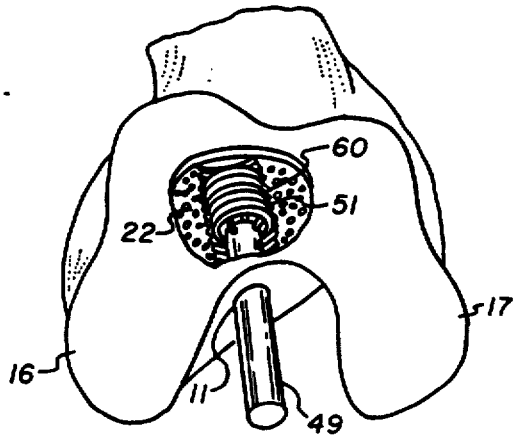
FIG. 11 shows a front elevation view of a fem ur that has a tunnel formed into the base cortex, showing a section of the bone removed to expose the end connector of FIGS. 8 through 10 turned therein.

FIG. 10 shows a threaded cylinder 50 that is a preferred configuration of a femoral attachment for an allograft ligament 49 for securing a ligament end in the femoral anterior cortex end of tunnel 11. Cylinder 50 is shown to have the appearance of a set screw, in that it is threaded at 51 along its entire length, as shown in FIG. 8 and 9, and includes a center hex-sided cavity 53. Additionally, the cylinder 50 preferably includes longitudinal holes 5-2 that are radially formed therethrough around the center hex-sided cavity 53. The cavity 53 is formed in a ligament attaching end of cylinder 50 that is preferably dished below a circumferential lip 54. The cylinder 50 is preferably fabricated of a biodegradable material such as a polylactic acid plastic or like material, to be absorbed by the body in the healing process. FIG. 10 shows an end of allograft ligament 49 being attached to cylinder 50 by passing a suture 56 at spaced intervals around the ligament end,. which suture is also selectively threaded through longitudinal passages 52 using a needle 57. The ligament end is then drawn tightly against the cylinder 50 dished out portion, fitting below the circumferential lip 54. Shown in FIGS. 10 and 10 A, for installation, the allograft ligament is unrolled and is wrapped around a hex-sided driver 58, which drive should be long enough to be turned from without the tunnel 11. The allograft ligament has an overlapping layered appearance, as shown in the sectional view of FIG. 10A. To install the hex-sided driver 58 the allograft ligament is unwrapped so as to loosen it as the center wherethrough the hex-sided driver if fitted. The ligament and driver are then fitted into tunnel 11 and the cylinder 50 threads 51 are turned into a tapped fem ur end 60 of tunnel 11. After seating of the cylinder, the hex-sided driver 58 is removed and the allograft ligament 49 stretched out, as illustrated in FIG. 11. The cylinder threads 51, are preferably machine type threads, as shown in FIGS. 8 through 11, and therefore thread 51 depth is not as great as is the depth of threads 41 of the prosthetic ligament 40 of FIG. 6. It should, however, be understood that the threaded femoral attachment end of the prosthetic ligament 40 and cylinder 50 can have the same or different depth of thread within the scope of this disclosure.

With cylinder 50 seated as described and the allograft ligament 49 stretched thereform, to complete the ligament reconstruction, the allograft ligament 49 is pulled tight so as to achieve a certain tensile loading thereon. The ligament tibial end is then secured to the tibia as by bending the ligament 49 tibial end across the bone surface from the tunnel 11 entry and is fixed thereat as by driving staples into the bone that span the ligament. Of course, a tibial attachment device such as a collar arrangement, that could be pinched around the ligament, not shown, or the like, can be used for attaching the allograft ligament tibial end to the tibia within the scope of this disclosure.

The above sets out the preferred end connector arrangements and system for their use for ligament reconstructive surgery as particularly applicable to a replacement of the anterior cruciate ligament with a prosthetic or allograft ligament. It should, however, be understood that the described procedures is and/or the devices described herein can be appropriately modified to be used to surgically replace the posterior cruciate ligament and/or other knee ligaments, within the scope of this disclosure. It should also be understood that any or all of the described ligament end connectors can be fabricated from a material or materials such as a polylactic acid plastic, or the like, to be absorbed by the body during the healing process. Obviously, however, the described connectors can be manufactured from an appropriate metal to remain in the bone after the healing process has taken place.

The present disclosure has, of course, been directed to both prosthetic and allograft ligaments. Within present technology, a prosthetic ligament manufactured by Zimmer U.S.A. is believed to be suitable for the described application. Approval for this ligament for use as an implant is currently being sought from the Food and Drug Administration for human implant. It should, however, be understood that the present invention is not limited to use with such particular prosthetic ligament only and that the end connection devices set out herein can be used with other prosthetic ligaments as may be now available or as may be developed in the future within the scope of this disclosure. Of course, allograft ligaments from cadavers are presently available for human implant.

The above described configurations of an allograft femoral device, shown as cylinder 50 in FIGS. 8 through 11, has been laboratory tested as set out in Table I hereinbelow. Table I shows the pull out strength of the femoral attachment component, the cylinder 50 that incorporates three (3) sutures 56 each threaded through and back through passage 52, securing the ligament end to the cylinder end. Each suture was capable of sustaining a twenty (20) pounds tensile load. The test standard thereby being that the attachment device, cylinder 50 and its suture connection would sustain at least a pull-out tensile stress of sixty (60) pounds. The test data in Table I shows that this criterior was met, the minimum sustained load shown as sixty seven (67) pounds. Additionally, it should be noted that all tests were performed using bones that came from specimens that were older than sixty (60) years at the time of death. The advanced age of the bone specimens used, it can be assumed, increases the chances that the bones will be softer and more porous, greatly reducing the bone strength. Test performed on younger bones, it can reasonably be assumed, would likely show greater failure strengths. Even using the aged specimens, the tests demonstrated the utility of the connector as the minimum load sustained of sixty seven (67) pounds was still greater than the combined suture strength of sixty (60) pounds, with the other tests for the different thread configurations showing much greater failure strength.

TABLE I

| | SPECIMEN SPECIFICATIONS | | | | | |
|---|---|---|---|---|---|---|
| Material Test Note Number | Date | Thread Length | Major Dia. | Minor Dia. | Threads Per Inch | Load (Lbs.) |
| 1 | 7-29-86 | .702 | .374 | .236 | 9 | 267 |
| 2 | 7-29-86 | .702 | .374 | .236 | 9 | 129 |
| 3 | 7-29-86 | .702 | .374 | .236 | 9 | 165 |
| 4 | 8-07-86 | 1.134 | .373 | .236 | 9 | 169 |
| 5 | 8-07-86 | .594 | .374 | .236 | 9 | 133 |
| 6 | 9-04-86 | .750 | .328 | .236 | 12 | 115 |
| 7 | 9-04-86 | .750 | .328 | .236 | 12 | 67 |
| 8 | 9-04-86 | .750 | .328 | .236 | 12 | 85 |
| 9 | 9-04-86 | .750 | .328 | .236 | 12 | 142 |
| 14 | 9-12-86 | .750 | .375 | .280 | 18 | 120 |
| 15 | 9-12-86 | .750 | .375 | .280 | 18 | 220 |
| 16 | 9-12-86 | .750 | .375 | .280 | 18 | 520 |
| 17 | 9-12-86 | .750 | .375 | .280 | 18 | 120 |

NOTE
MATERIAL TEST NOTE NUMBER 10-13 INVOLVE TIBIAL ATTACHMENT DEVICES AND DO NOT APPLY

Herein has been set out a preferred surgical procedure or system and ligament end attachement devices. It should, however, be understood that the present disclosure is made by way of example only and that variations to the procedure or system and the described ligament end connectors are possible without departing from the subject matter coming within the scope of the following claims, which claims we regard as our invention.

We claim:

1. A surgical system for implanting a human knee joint ligament, particularly a cruciate ligament comprising, under fluoroscopic control and with the patient's leg bent and maintained appropriately, at single incision to the tibial tuberosity, urging a guidewire through the bone surface and passing through the cruciate ligament junctions to the proximal tibia and distal fem ur, the guidewire further urged into the fem ur cortex, which guidewire is to receive and guide therealong successively larger drills to form a ligament tunnel of a diameter to accommodate a selected allograft or prosthetic ligament, and the end of which ligament tunnel within said fem ur cortex is further prepared to receive a ligament fem ur attachment connector fitted and secured therein; an allograft or prosthetic ligament for implant in said ligament tunnel that includes on one end the femoral attachment connector and is arranged for insertion into said ligament tunnel, the femoral attachment connector arranged for perm anent installation in said fem ur cortex at said ligament tunnel end; and securing a tibial attachment end of said ligament at the open tibia end of said ligament tunnel.

2. A surgical system as recited in claim 1, wherein for replacement of an anterior cruciate ligament, the patient's leg is bent and maintained at approximately a ninety degree (90°) angle and the incision is made medial to the tibia tuverosity down to a point on the bone surface that is approximately two (2) centimeters distant from the medial tibial plateau; and the guidewire is inserted into the tibia at that point to travel through the joint to cross the intercondylar notch area and engage the fem ur posterior and lateral femoral condyle at a point within said intercondyalr notch area that is approximately four (4) millimeters anterior to the junction of the fem ur posterior cortex and the intercondylar seam, the guidewire entering the fem ur to pass through the cancellous bone that surrounds the medullary channel is passed through the medullary channel and into the fem ur anterior lateral cortex.

3. A surgical system as recited in claim 1, wherein the ligament tunnel end within the fem ur cortex is drilled by turning a flaring drill means therein so as to form an open inverted cone shaped section.

4. A surgical system as recited in claim 3, wherein the ligament femoral attachment connector is an expansion cone formed as an open cylinder having a proximal end connected to an end of a prosthetic ligament that includes an open center longitudinal passage therethrough, which expansion cone is longitudinally slotted at spaced apart intervals around its distal end from said prosthetic ligament and includes a continuous groove formed around the cylinder inner circumference; and an arrangement for expanding said expansion cone into a skirt at its longitudinally slotted end to conform to the inverted cone shape section formed at the ligament fem ur cortex end.

5. A surgical system as recited in claim 4, wherein the arrangement for expanding the expansion cone consists of a cylindrical expansion anchor that is center holed on one end and receives an end of a rod that is releasably secured therein so as to be capable of breaking away when a certain pulling force is exerted thereon, which rod is telescoped through said prosthetic ligament open center longitudinal passage, the opposite rod end extending beyond said prosthetic ligament end for receiving a pulling force thereon to move said expansion anchor into said expansion cone so as to flare said expansion cone outwardly into a skirt at said longitudinal slots, a circumferential edge formed around said expansion anchor to travel into the continuous groove of the inner circumference of the expansion cone, locking therein.

6. A surgical system as recited in claim 5, wherein the expansion anchor tapers inwardly from a central ring to a lesser diameter section and then outwardly to the end wherein the expansion anchor is center holed forming a circumferential edge that is the same diameter as the expansion anchor center portion; and the expansion anchor center hole is tapped to receive a threaded end of the rod, which rod and expansion anchor center hole threads are such as to disengage when a certain tension stress is applied therebetween.

7. A surgical system as recited in claim 3, wherein, to provide for securing the prosthetic ligament tibial attachment end to the tibia, a flattened cone shaped disk is provided having a lesser diameter end wherefrom the cone shaped disk outer surface slopes uniformly outwardly to a greater diameter end, which lesser diameter end is for alignment with and installation in the tibia end of the ligament tunnel, the cone shaped disk having a center opening therethrough that is tapped to be turned over a threaded tibial end of said prosthetic ligament, turning of which cone shaped disk on said prosthetic ligament threaded end to move said lesser diameter cone shaped disk end into engagement with the bone around said ligament tunnel tibial end for setting prosthetic ligament tensioning.

8. A surgical system as recited in claim 1, wherein the ligament tunnel closed end within the fem ur cortex is tapped to form threads in the surrounding bone.

9. A surgical system as recited in claim 8, wherein, for a prosthetic ligament, the ligament femoral attachment connector includes thread means formed on the prosthetic ligament fem ur end for turning into the threads formed in the ligament tunnel at the fem ur cortex end.

10. A surgical system as recited in claim 8, further includes, for securing the prosthetic ligament tibial attachment end to the tibial end of the ligament tunnel, a flattened cone shaped disk having a lesser diameter end wherefrom the cone shaped disk slopes uniformly outwardly to a greater diameter end, which lesser diameter end is for alignment with and installation in the tibia end of the ligament tunnel, the cone shaped disk having a center opening therethrough that is tapped to be turned over a threaded tibial end of said prosthetic ligament, turning of which cone shaped disk on said prosthetic ligament to move said lesser diameter cone shaped disk end into engagement with the bone around said ligament tunnel tibial end for setting prosthetic ligament tensioning.

11. A surgical system as recited in claim 8, wherein, for an allograft R ligament, the fem ur attachment connector is a cylinder that includes threads formed along the length of its outer circumference, which threads are for turning into the threads formed in the fem ur cortex end of the ligament tunnel, which fem ur attachment connector is holed longitudinally from end to end at radial spaced apart intervals to accommodate a suture that is threaded therethrough and through spaced points at the end of the allograft ligament, the cylinder further including a center longitudinal sided driver hole formed in one end thereof; and a tool that is sided to fit within the cylinder center longitudinal sided driver hole, wherearound the allograft ligament is arranged for turning said cylinder into the threaded fem ur cortex end of the ligament tunnel, the tool opposite end to extend out from the tibia end of said ligament tunnel for turning.

12. A surgical system as recited in claim 11, wherein the one end of the fem ur attachment connector is dished inwardly at the allograft ligament connection end, a circumferential lip extending from the cylinder end above that dished out portion to accommodate the end of said allograft ligament drawn therepast, against the dished surface of the cylinder, by tightening the sutures that have been passed at intervals through the allograft ligament end and threaded through through the cylinder radial longitudinal holes.

13. A surgical system as recited in claim 11, wherein the center longitudinal hole is hexagonally sided to accommodate, as the tool, a straight hexagonally sided shaft for sliding into said cylinder center longitudinal hole and accommodating the allograft ligament arranged therearound.

14. A surgical system as recited in claim 1, wherein the respective fem ur cortex and tibial attachment connectors of the prosthetic and allograft ligaments are formed of a biodegradable material for absorption by the body.

15. A surgical system as recited in claim 1, wherein the biodegradable material is polylactic acid.

16. A surgical system for a prosthetic ligament implant as a replacement for a knee ligament, particularly a cruciate ligament, the ligament for installation in a ligament tunnel formed to have a closed end in either the femoral or tibial cortex, said ligament tunnel extending across the knee joint and is open at the distal bone surface from the ligament tunnel closed end, which ligament tunnel closed end is prepared to receive and connect in binding engagement to an end of said prosthetic ligament comprising, a femoral attachment connector end means secured to one end of said prosthetic ligament to be permanently secured in said prepared ligament tunnel cortex end; and a tibial attachment connector means that is secured to said prosthetic ligament other end for maintaining and adjusting the prosthetic ligament tensioning at the ligament tunnel entrance which tibial attachment connector means consists of a flattened cone shaped disked that has a lesser diameter end wherefrom the cone shaped disk outer surface slopes uniformly outwardly to a greater diameter end, which lesser diameter end is for alignment with and installation in the open end of said ligament tunnel, the cone shaped disk having a center opening therethrough that is tapped to be turned over a threaded end of said prosthetic ligament, turning of which cone shaped disk on said prosthetic ligament threaded end to move said lesser diameter cone shaped disk end into engagement with the bone around said ligament tunnel open end.

17. A surgical system for a prosthetic ligament implant as recited in claim 16, wherein the ligament tunnel closed end is formed to have an open inverted cone shaped section and the femoral attachment connector means is an expansion cone that is formed as an open cylinder, is longitudinally open therethrough and has a proximal end that is secured to an end of the prosthetic ligament, which prosthetic ligament includes an open center longitudinal passage therethrough, and the expansion cone is longitudinally slotted at spaced apart intervals around its distal end from its coupling to said prosthetic ligament end and includes a continuous groove formed around the cylinder inner circumference at approximately the center thereof; and means for expanding said expansion come into a skirt at its longitudinally slotted end.

18. A surgical system as recited in claim 17, wherein the means for expanding the expansion cone consists of an expansion anchor means that is cylindrical in shape and is center holed on one end to receive an end of a rod releasably secured, which coupling is such so as to be capable of breaking apart when a certain pulling force is exerted thereon, which rod is telescoped in sliding arrangement through said prosthetic ligament open center longitudinal passage the opposite rod end extending beyond said prosthetic ligament end; and said expansion anchor means to travel on the end of said rod into said expansion cone a circumferential edge of said expansion anchor means to travel into the continuous groove that is formed around the inner circum ference of said expansion cone to flare said expansion cone outwardly into a skirt at said longitudinal slots and locking therein.

19. A surgical system as recited in claim 18, wherein the expansion anchor tapers inwardly from a central ring to a lesser diameter section and then outwardly to the end wherein the expansion anchor in center holded forming a circumferential edge that is the same diameter as the expansion anchor center portion; and the expansion anchor center hole is tapped to receive a threaded end of the rod, which rod and expansion anchor center hole threads are such as to disengage when a certain tension stress is applied therebetween.

20. A surgical system for a prosthetic ligament implant as recited in claim 16, wherein the ligament tunnel closed end is tapped to form threads in the surrounding bone and the end means of the prosthetic ligament for perm anent atttachment in that ligament tunnel closed end includes thread means formed therearound for turning into the threads formed in said closed end of the ligament tunnel.

21. A surgical system for a prosthetic ligament as recited in claim 16, wherein the respective prosthetic ligament attachment connector means are formed of a biodegradable material for absorption by the body.

22. A surgical system for a prosthetic ligament as recited in claim 21, wherein the biodegradable material is polylactic acid.

23. A surgical system for installing an allograft ligament implant as a replacement for a knee ligament, particularly a cruciate ligament, the ligament for installation in a straight ligament tunnel formed to have a closed end in either the femoral or tibial cortex, which ligament tunnel extends across the knee joint and is open at the distal bone surface from the ligament tunnel closed end, the ligament tunnel closed end to be tapped to form threads in the surrounding bone comprising, as an allograft ligament connector, a cylinder that has threads formed over its length around its outer circumference, which threads are for turning into the threads formed in the threaded closed end of the ligament tunnel, which cylinder is holed longitudinally from end to end at radial spaced apart intervals to accommodate a suture that is threaded therethrough and through spaced points at the end of the allograft ligament, said cylinder further including a center longitudinal sided driver hole formed in one end thereof; sided tool means appropriate for removable fitting into said center longitudinal sided driver hole for turning said cylinder into said ligament tunnel threaded said tool means opposite end to extend from the open end of said ligament tunnel; and the unattached allograft ligament end is bent into engagement with the bone at said ligament tunnel open end to receive connector means for securing said ligament end to said bone surface.

24. A surgical system for installing an allograft ligament as recited in claim 2, wherein the one end of the allograft ligament connector is dished inwardly and includes a circumferential lip that extends above said dished portion to accommodate the end of said allograft ligament drawn therein by tightening the sutures that have been passed therethrough and through the cylinder radial longitudinal holes.

25. A surgical system as recited in claim 23, wherein the cylinder center longitudinal hole is hexagonally sided to accommodate, as the tool means, a straight hexagonally sided shaft for sliding into said cylinder center longitudinal hole and accommodating the allograft ligament arranged therearound.

26. A surgical system as recited in claim 23, wherein the allograft ligament connector is formed of a biodegradable material for absorption by the body.

27. A surgical system as recited in claim 25, wherein the biodegradable material is polylactic acid.

*28. A surgical system for replacement of an anterior cruciate ligament comprising, with the pateint's knee bent appropriately, from a single skin incision at the proximal tibial, means for forming a bone tunnel passes through the proximal tibia. through the cruciate ligament junctions, and into the endosteal bone within distal fem ur; a graft ligament, either natural or prosthetic, that includes a mounting means installed onto its femoral end, said ligament adapted to be arthroscopically installed into said distal fem ur bony tunnel; means for endosteally securing said mounting means in said distal fem ur tunnel; and means for securing, under tension, the other end of said graft ligament at or adjacent to the proximal tibial cortex tunnel end.*

*29. A surgical system as recited in claim 28, wherein the system is practiced under fluoroscopic visualization control.*

*30. A surgical system as recited in claim 28, wherein the mounting means is introduced to the intra articular opening of the femoral tunnel through the tibial tunnel or through an adjacent soft tissue portal formed into the knee joint.*

*31. A surgical method for performing ligament surgery comprising the steps of bending the tibia to a predetermined angle with respect to the fem ur, forming a straight ligament tunnel through the tibia and into the fem ur, via a single proximal tibia incision, and securing ends of a natural of prosthetic ligament, respectively, to the tibia and endosteally within the distal fem ur portion of said tunnel.*

*32. A surgical method as recited in claim 31, wherein the natural or prosthetic ligament end is endosteally fixed within the distal fem ur by use of an attachment device connected to the ligament end which provides for ligament fixati0n within the distal fem ur portion of the tunnel; setting the ligament tension at the open end of the tibial ligament tunnel; and securing said ligament tibial end at or adjacent to said open ligament tunnel tibial end.*

*33. A surgical method as recited in claim 31, wherein the ligament tunnel is drilled from a single incision at the anterior medial tibia.*

*34. A surgical method as recited in claim 31, wherein the ligament femoral end is secured within the distal femoral tunnel portion between the distal fem ur posterior and anterior cortexes.*

*35. A surgical method as recited in claim 31, wherein the ligament femoral end includes an attachment device that is introduced into the ligament tunnel through the open tibial tunnel end or through an adjacent soft tissue portal into the knee joint.*

* * * * *

UNITED STATES PATENT AND TRADEMARK OFFICE

CERTIFICATE OF CORRECTION

PATENT NO. : Re.34,293

DATED : June 22, 1993

INVENTOR(S) : E. Marlowe Goble and W. Karl Somers

It is certified that error appears in the above-indentified patent and that said Letters Patent is hereby corrected as shown below:

The word "femur" is incorrectly spelled throughout the patent. Accordingly, the word "fem ur" should be corrected to —femur— as found in:

| Column | Rows |
|---|---|
| 1 | 36,43,62 |
| 2 | 14,42,43,48,49 |
| 3 | 8,20,60,68 |
| 4 | 1,4,12,59,60,65 |
| 5 | 15,21,29,39,53,66 |
| 6 | 46,48,50,58,62,63,68 |
| 7 | 8,19,22,23,34,43,46,48,32 |
| 9 | 43,46 |
| 12 | 5,6,11,12,18,30,34,37,39,54,55,33 |
| 13 | 30,35,36,54,57,58,67 |
| 14 | 4,20 |
| 16 | 27,31,43,44,47,50,52,61,30 |

In the Abstract, line 7, after the word "Tuberosity", delete "," and add —.—.

Column 2, line 39, after the word "tuberosity.", delete "Form" and add —From—.

Column 4, line 9, after the word "tunnel" delete "form ation" and add —formation—.

Column 5, line 63, after the word "possible" add —,—.

UNITED STATES PATENT AND TRADEMARK OFFICE

CERTIFICATE OF CORRECTION

PATENT NO. : Re.34,293

DATED : June 22, 1993

INVENTOR(S) : E. Marlowe Goble and W. Karl Somers

It is certified that error appears in the above-indentified patent and that said Letters Patent is hereby corrected as shown below:

In Column 16, line 52, delete the first word "fixati0n" and add --fixation--.

Signed and Sealed this

Seventh Day of February, 1995

Bruce Lehman

*Attest:*

BRUCE LEHMAN

*Attesting Officer*

*Commissioner of Patents and Trademarks*

US001034293B1

REEXAMINATION CERTIFICATE (3472nd)

United States Patent [19]

[11] B1 Re. 34,293

Goble et al.

[45] Certificate Issued Apr. 7, 1998

[54] LIGAMENT ATTACHMENT METHOD AND APPARATUS

[75] Inventors: E. Marlowe Goble, 1414 E. 1220 North, Logan, Utah 84321; W. Karl Somers, Logan, Utah

[73] Assignee: E. Marlowe Goble, Utah

Reexamination Request:
No. 90/004,506, Jan. 6, 1997

Reexamination Certificate for:

| | |
|---|---|
| Patent No.: | **Re. 34,293** |
| Issued: | **Jun. 22, 1993** |
| Appl. No.: | **529,319** |
| Filed: | **May 29, 1990** |

Certificate of Correction issued Feb. 7, 1995.

Related U.S. Patent Documents

Reissue of:

| | | |
|---|---|---|
| [64] | Patent No.: | **4,772,286** |
| | Issued: | **Sep. 20, 1988** |
| | Appl. No.: | **15,432** |
| | Filed: | **Feb. 17, 1987** |

[51] Int. Cl.[6] ..... A61F 1/00

[52] U.S. Cl. ..... 623/13

[58] Field of Search ..... 623/13, 16; 606/72, 606/73, 80, 88, 96, 97

[56] References Cited

U.S. PATENT DOCUMENTS

| | | | |
|---|---|---|---|
| 3,953,896 | 5/1976 | Treace et al. | 623/13 |
| 3,973,277 | 8/1976 | Semple et al. | 623/13 |
| 4,301,551 | 11/1981 | Dore et al. | 623/13 |
| 4,400,833 | 8/1983 | Kurland . | |

OTHER PUBLICATIONS

"Intraarticular Semitendinosus Anterior Cruciate Ligament Reconstruction" by Robert C. Hendler, M.D. Surgical Management of Cruciate and Collateral Ligament.

"A Unitunnel Technique for Arthroscopic Anterior Cruciate Ligament Reconstruction" by Robert C. Hendler, M.D.

"A unitunnel technique for arthroscopic anterior cruciate ligament reconstruction" by Robert C. Hendler, MD published in Techniques IN, vol. 2, No. 4.

Patients's records for first performed Hendler surgical procedure employing his new techniques.

Instruction Manual concerning tools manufactured by Richard Wolf Company for practicing the Hendler procedure.

Brochure from Richard Wolf Company describing tools manufactured and sold for practicing the Hendler procedure.

Videotape label and accompanying videotape put out by Richard Wolf Medical Instruments Corporation that is included with purchase of instruments.

(List continued on next page.)

*Primary Examiner*—David T. Isabella

[57] ABSTRACT

The invention provides a system for surgically implanting an allograft or prosthetic ligament as a replacement for a patient's cruciate ligaments. In a practice of the system, as a replacement for an anterior cruciate ligament, the patient's leg is bent and maintained at approximately a ninety degree (90°) angle, a single incision is made medial to the tibial tuberosity. From this incision, under fluoroscopic and arthroscopic control, a guidewire is driven through the tibia and across the cruciate ligament junctions with the proximal tibia and distal femur ends and into the femur cortex. Succesively larger drills are then turned along the guidewire to form a ligament tunnel, with, as a last step in the tunnel formation process, the preparation of the femur cortex end of the tunnel to receive a femoral connector of the implanted ligament, which connector is arranged in one embodiment to be outwardly flared and in another embodiment to be turned into the appropriately prepared femur end of the ligament tunnel to lock therein. The invention, in addition to the embodiment of the ligament femur end connectors, further includes a tibial surface ligament tibial end connector for both securing the ligament end to the bone and the setting ligament tensioning, of which ligament connectors can be manufactured from a biodegradable material for absorption by the body.

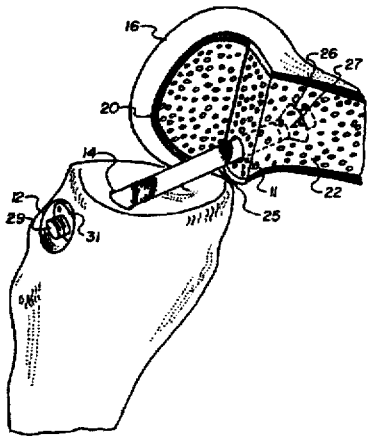

OTHER PUBLICATIONS

Arthroscopic Surgery Principles & Practice by Lanny L. Johnson, M.D., vols. One and Two, Third Edition, pp. 654, 1159, and 1160.

"A Modified Technique for Anterior Cruciate Ligament (ACL) Surgery Using a New Drill Guide for Isometric Positioning of the ACL" by Odensten & Gillquist.

"Functional Anatomy of the Anterior Cruciate Ligament and a Rationale for Reconstruction" by Magnus Odensten, M.D., Ph.D. and Jan Gillquist, M.D., Ph.D.

Text Material Arthroscopic Surgery: Principles and Practice "Ligaments and Tendons".

Text Material Chapter 12, Extrasynovial Conditions, pp. 1101–1238.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4–27 is confirmed.

Claims 1, 3, 28, 31 and 34 are determined to be patentable as amended.

Claims 2, 29, 30, 32, 33 and 35, dependent on an amended claim, are determined to be patentable.

1. A surgical system for implanting a human knee joint ligament, particularly a cruciate ligament comprising, under fluoroscopic control and with the patient's leg bent and maintained appropriately, at single incision to the tibial tuberosity, urging a guidewire through the bone surface and passing through the cruciate ligament junctions to the proximal tibia and distal femur, the guidewire further urged into the femur cortex, which guidewire is to receive and guide therealong successively larger drills to form a ligament tunnel of a diameter to accommodate a selected allograft or prosthetic ligament, and the end of which ligament tunnel within said femur cortex is *closed or is blind and is* further prepared to receive a ligament femur attachment connector fitted and secured therein[:]; an allograft or prosthetic ligament for implant in said ligament tunnel that includes on one end the femoral attachment connector and is arranged for permanent installation in said femur cortex at said ligament tunnel *closed or blind* end; and [securing] a tibial attachment end of said ligament *is secured* at the open tibia end of said ligament tunnel.

3. a Surgical system as recited in claim 1, wherein the ligament tunnel *adjacent to the closed or blind* end within the femur cortex is drilled by turning a flaring drill means therein so as to form as open inverted cone shaped section.

28. A surgical system for replacement of an anterior cruciate ligament comprising, with the patient's knee bent appropriately, from a single skin incision at the proximal tibial, means for forming a bone tunnel [passes] *passed* through the proximal tibia, through the cruciate ligament junctions, and into the endosteal bone, *terminating in a closed or blind tunnel end* within the distal femur; a graft ligament, either natural or prosthetic, that includes a mounting means installed onto its femoral end, said ligament adapted to be arthroscopically installed into said distal femur bony tunnel; means for endosteally securing said mounting means in said distal femur tunnel *adjacent to said closed off blind tunnel end and* at a distance from the femoral tunnel end at the distal femur posterior that is greater than two (2) centimeters; and means for securing, under tension, the other end of said graft ligament at or adjacent to the proximal tibial cortex tunnel end.

31. A surgical method for performing ligament surgery comprising the steps of bending the tibia to a predetermined angle with respect to the femur, forming a straight ligament tunnel through the tibia and into the femur *to a closed or blind tunnel end* via a single proximal tibia incision, and securing ends of a natural or prosthetic ligament, respectively, to the tibia and endosteally within the distal femur portion of said tunnel *at a location adjacent to the closed or blind tunnel end and* at a distance from the femoral tunnel end at the distal femur posterior that is greater than two (2) centimeters.

34. A surgical method as recited in claim 31, wherein the ligament femoral end is secured within the distal femoral tunnel *adjacent to the closed or blind tunnel end* portion between the distal femur posterior and anterior cortexes where said ligament femoral end is closer to said femur lateral cortex surface adjacent to said femoral *closed or blind* tunnel end in the femur endosteum than to said distal femur posterior.

* * * * *